United States Patent

YHaslanger et al.

[11] 4,456,616
[45] Jun. 26, 1984

[54] 7-OXABICYCLOHEPTANE SUBSTITUTED AMINO PROSTAGLANDIN ANALOGS AND THEIR USE IN INHIBITING PLATELET AGGREGATION AND BRONCHOCONSTRICTION

[75] Inventors: Martin F. YHaslanger, Lambertville; Masami Nakane, Hopewell; Steven E. Hall, Ewing Township, Mercer County, all of N.J.

[73] Assignee: E. R. Squibb & Sons, Inc., Princeton, N.J.

[21] Appl. No.: 453,849

[22] Filed: Dec. 27, 1982

[51] Int. Cl.³ .................... A61K 31/34; C07D 307/00
[52] U.S. Cl. .................................... 424/285; 549/463
[58] Field of Search ...................... 549/463; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 32292 6/1982 European Pat. Off.
2039909 8/1980 United Kingdom.

*Primary Examiner*—Henry R. Jiles
*Assistant Examiner*—Bernard Dentz
*Attorney, Agent, or Firm*—Lawrence S. Levinson; Burton Rodney

[57] ABSTRACT

7-Oxabicycloheptane substituted amino prostaglandin analogs are provided having the structural formula

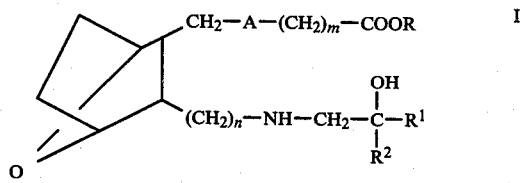

and including all stereoisomers thereof.

The compounds are cardiovascular agents useful, for example, in the treatment of thrombolytic disease.

13 Claims, No Drawings

7-OXABICYCLOHEPTANE SUBSTITUTED AMINO PROSTAGLANDIN ANALOGS AND THEIR USE IN INHIBITING PLATELET AGGREGATION AND BRONCHOCONSTRICTION

DESCRIPTION OF THE INVENTION

The present invention relates to 7-oxabicycloheptane substituted amino prostaglandin analogs which are cardiovascular agents useful, for example, in the treatment of thrombolytic disease. These compounds have the structural formula

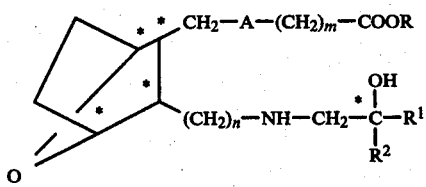

and including all stereoisomers thereof, wherein

A is $CH=CH$ or $(CH_2)_2$, m is 1 to 8, n is 0 to 5, R is H or lower alkyl; and $R^1$ and $R^2$ are the same or different and may be hydrogen, lower alkyl, aryl, aralkyl, cycloalkyl, cycloalkylalkyl or $-CH_2-X-R^3$ wherein X is O or S and $R^3$ is lower alkyl, aryl or aralkyl, with the proviso that at least one of $R^1$ and $R^2$ is other than hydrogen.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halosubstituent, such as F, Br, Cl or I or $CF_3$, an alkoxy substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl", "aryl-lower alkyl" or "cycloalkylalkyl" as used herein refers to lower alkyl groups as discussed above having an aryl substituent, such as benzyl or a cycloalkyl substituent.

The terms "$(CH_2)_m$" and "$(CH_2)_n$" includes a straight or branched chain radical having from 1 to 8 carbons in the normal chain in the case of "$(CH_2)_m$" and 0 to 5 carbons in the normal chain in the case of "$(CH_2)_n$" and may contain one or more lower alkyl substituents. Examples of $(CH_2)_m$ and $(CH_2)_n$ groups include $CH_2$, $CH_2CH_2$, $(CH_2)_3$, $(CH_2)_4$, $(CH_2)_5$, $(CH_2)_6$, $(CH_2)_7$,

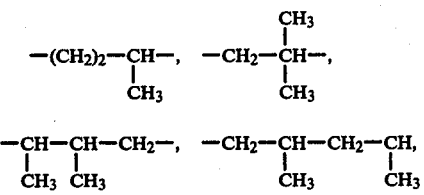

and the like.

Preferred are those compounds of formula I wherein A is $(CH_2)_2$ or $CH=CH$, m is 2 to 4, R is H, n is 0 or 1, $R^1$ is H, and $R^2$ is n-butyl, pentyl, hexyl or heptyl.

The various compounds of the invention may be prepared as outlined below.

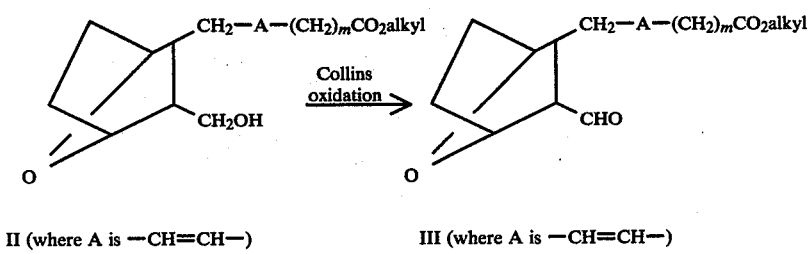

II (where A is $-CH=CH-$)   III (where A is $-CH=CH-$)

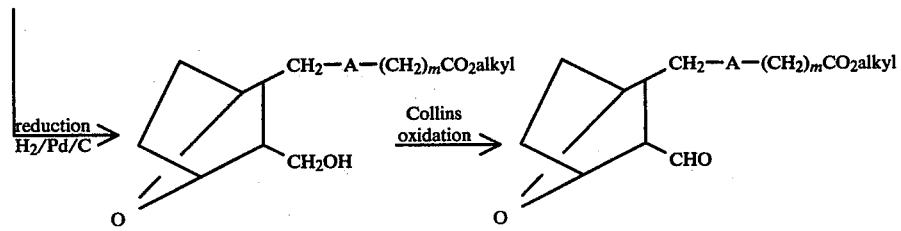

IIA (where A is $-(CH_2)_2-$)   IIIA (where A is $-(CH_2)_2-$)

Where n is 1
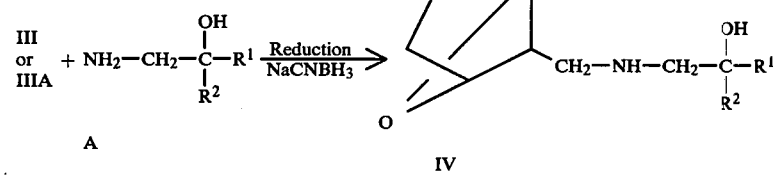
↓ Hydrolysis
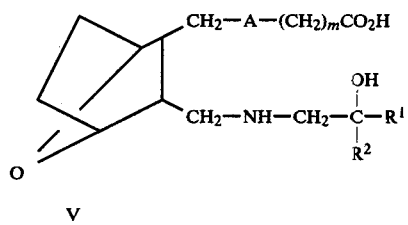
V
Where n is 2 to 5
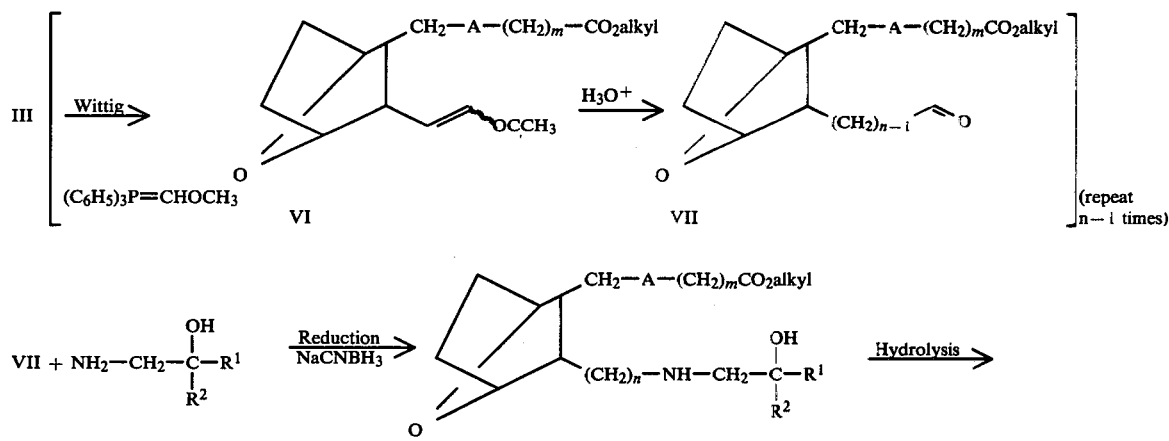
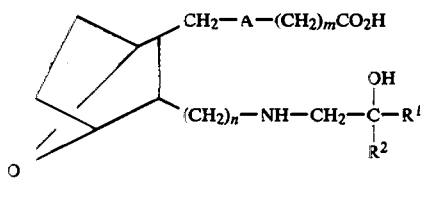
VA
Where n is 0
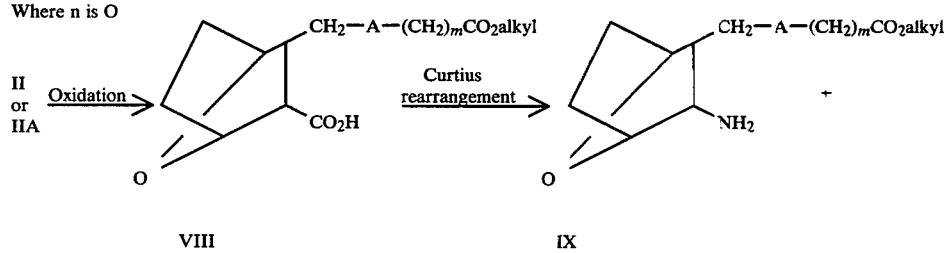

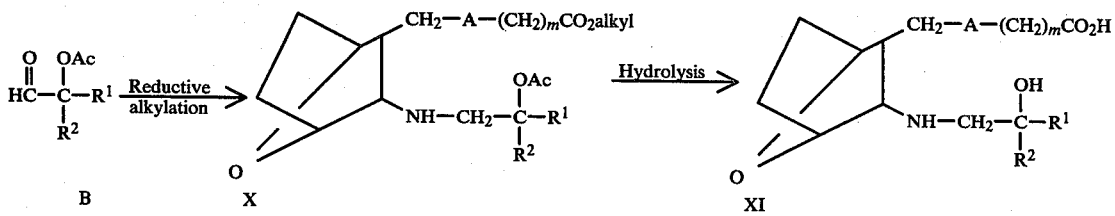

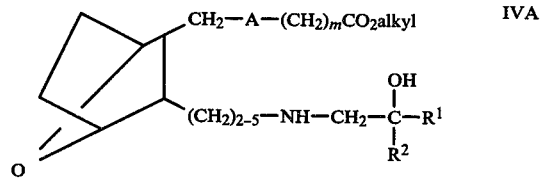

In the reaction sequence identified as "A", the starting lower alkyl ester containing the hydroxymethyl group, that is, compound II, (prepared as described in U.S. Pat. No. 4,143,054) is used to form the aldehyde III (where A is —CH=CH—) or IIIA (where A is —(CH$_2$)$_2$). Thus, to form aldehyde III where A is —CH=CH—, compound II is subjected to a Collins oxidation, for example, by reacting II with chromium trioxide in pyridine. To form the aldehyde IIIA (where A is (CH$_2$)$_2$), compound II is reduced, for example with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$).

As seen in reaction sequence "B", compounds of the invention where n is 1 that is

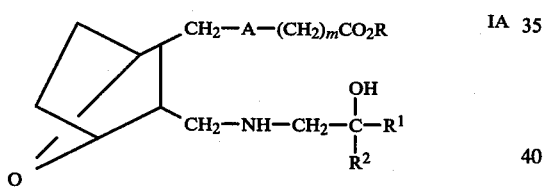

are prepared by reacting aldehyde III or IIIA with an aminoalcohol (A) employing a molar ratio of III or IIIA:aminoalcohol of within the range of from about 0.8:1 to about 1:1, in a solvent such as methanol or ethanol and a reducing agent such as sodium borohydride or sodium cyanoborohydride.

The reaction sequence identified as "C" is employed to prepare compounds of the invention wherein n is 2 to 5, that is,

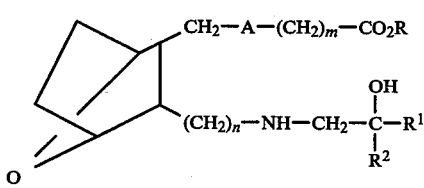

The aldehyde III or IIIA is used to prepared aldehyde VII (where n is 2-5) by carrying out a homologation sequence, such as a Wittig reaction with (C$_6$H$_5$)$_3$P=CHOMe followed by hydrolysis, (n-1) times. The aldehyde VII (where n is 2-5) is thus carried on to compounds of this invention where n is 2-5, that is

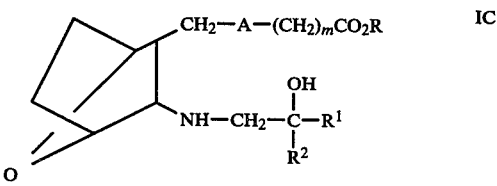

by reductive amination employing an amino alcohol A in a solvent such as methanol and a reducing agent such as sodium borohydride or sodium cyanoborohydride. Compound IV A may then be hydrolyzed to the corresponding acid VA.

In the reaction sequence identified as "D", compounds of the invention wherein n is 0, that is

[structure IC]

are prepared by oxidizing hydroxymethyl compound II or IIA, such as by reacting II or IIA with an oxidizing agent, such as pyridinium dichromate in a solvent, such as dimethylformamide, to form the acid VIII. Acid VIII is subjected to a Curtius rearrangement reaction which involves reacting acid VIII with carbonyldiimidazole in the presence of an inert organic solvent, such as toluene under an inert atmosphere, followed by addition of trimethylsilylazide to the reaction mixture and the resulting isocyanate solution is converted to the amine IX by reacting same with hydrochloric acid. The amine IX is subjected to reductive alkylation by reacting same with aldehyde B in a solvent, such as methanol and then adding sodium borohydride or other reducing agent, such as sodium cyanoborohydride in the presence of acetic acid to form the ester compound X which may be hydrolyzed to the corresponding acid XI.

The aminoalcohol starting materials of formula A are known in the art and may be prepared by conventional procedures or are commercially available. For example, where each of R$^1$ and R$^2$ in the formula A aminoalcohol is other than H, such compounds may be prepared according to the following reaction sequence:

-continued

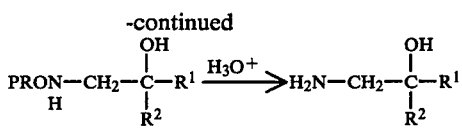

Where in the formula A compounds one of $R^1$ and $R^2$ is H, such compounds may be prepared according to the following reaction:

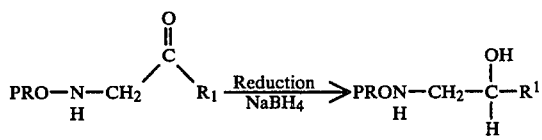

Where in formula A one of $R^1$ and $R^2$ is $CH_2R^4$ (where $R^4$ is lower alkyl, aryl, aralkyl or cycloalkyl) such compounds may be prepared according to the following reaction sequence.

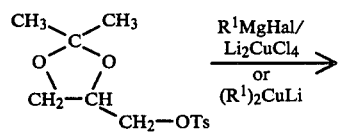

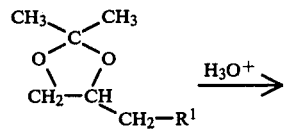

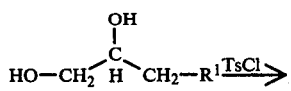

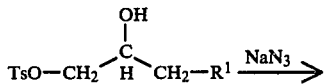

Where in the formula A compounds, $R^1$ or $R^2$ is $-CH_2-X-R^3$, such compounds may be prepared according to the following reaction sequence:

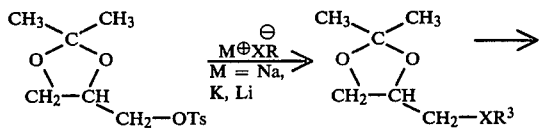

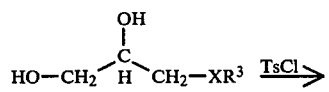

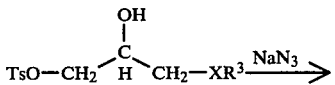

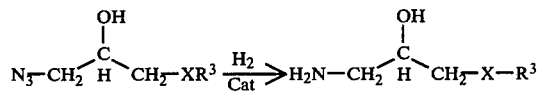

The aldehyde acetate starting material (B) employed in reaction sequence "D" may be prepared according to the following reaction sequence:

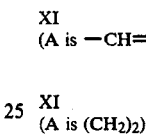
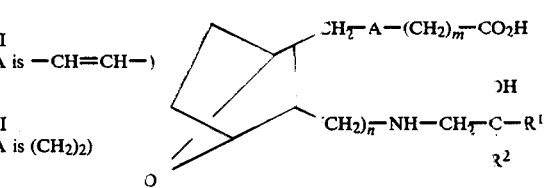

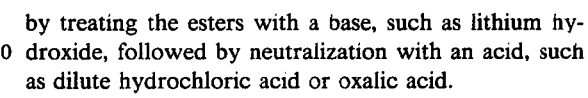
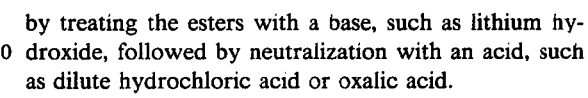

The esters can be converted to the free acid, that is, to

XI
(A is $-CH=CH-$)

XI
(A is $(CH_2)_2$)

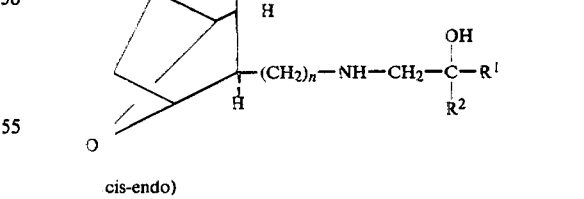

by treating the esters with a base, such as lithium hydroxide, followed by neutralization with an acid, such as dilute hydrochloric acid or oxalic acid.

The compounds of this invention may have four or five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

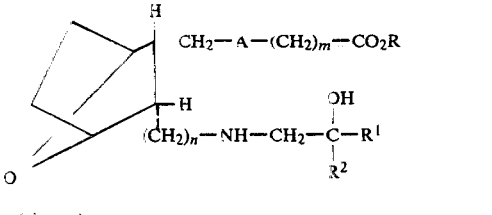

cis-endo)

cis-exo)

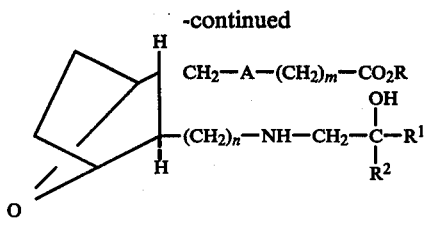

(trans)

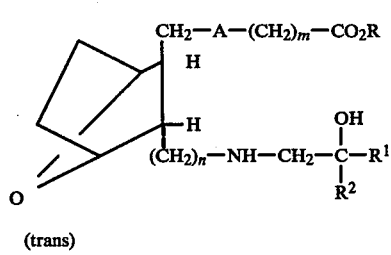

(trans)

The nucleus in each of the compounds of the invention is depicted as

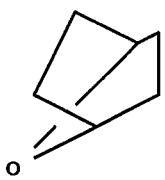

for matter of convenience; it will also be appreciated that the nucleus in the compounds of the invention may be depicted as

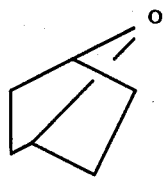

The compounds of this invention inhibit arachidonic acid-induced platelet aggregation and bronchoconstriction.

The compounds of this invention are cardiovascular agents useful as platelet aggregation inhibitors, e.g., for treatment of thrombolytic disease, such as coronary or cerebral thromboses. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following Examples represent preferred embodiments of this invention.

EXAMPLE 1

[1β,2α(5Z),3α,4β]-7-[3-[[(2-Hydroxyhexyl)amino]methyl]-7-oxabicyclo[2.2.1]hept-2-yl]-5-heptenoic acid, methyl ester

A. Tosylate of Solketal

A solution of distilled solketal (19.8 g, 0.15M) in pyridine (40 ml) was cooled in an ice bath in an argon atmosphere. A solution of tosyl chloride (34.3 g, 0.18M) in $CH_2Cl_2$ (80 ml) was added dropwise over a period of 1 hour to the above stirred solution. Stirring was continued for 3.5 hours at 0° C. and the mixture was then poured into ice water (500 ml). After stirring 30 minutes the layers were separated. The aqueous layer was extracted with EtOAc (3×300 ml). The combined organic layers ($CH_2Cl_2$ and EtOAc) were washed with 1N HCl (2×300 ml), saturated $NaHCO_3$ solution (2×300 ml) and water (1×300 ml). The solution was dried ($MgSO_4$) and freed of solvent in vacuo leaving the title tosylate as a waxy solid (40 g, 93% yield). TLC: $Et_2O$-Pet ether 1:1, UV & $I_2$:$R_f$=0.36.

B. Acetonide of 1,2-dihydroxyheptane n-Propyl magnesium bromide was prepared from 3.6 g (150 mmol) magnesium and 14.7 g (120 mmol) distilled n-propyl bromide in 100 ml distilled THF in an argon atmosphere. After all the bromide had been added, the mixture was heated under reflux for 45 minutes. The Grignard solution was then cooled to −78° C. and a solution of tosylate from Part A (14.3 g, 50 mmol) in THF (50 ml) was added dropwise. A solution of $Li_2CuCl_4$ in THF [10 ml of solution prepared by dissolving dry LiCl (0.85 g, 0.02M) and anhydrous $CuCl_2$ (1.34 g, 0.01M) in THF (100 ml)] was added. The mixture was allowed to warm slowly to room temperature and left stirring overnight. The mixture was poured into ice water (500 ml) and 1N HCl (100 ml). The product was extracted into ether (4×200 ml). The combined ether extracts were washed with water (1×250 ml), dried ($MgSO_4$) and freed of solvent in vacuo leaving 13.6 g oil. This was chromatographed on silica gel 60 (300 g). The desired title B compound was eluted with ether-pentane 1:5 to give 1.87 g (24%). Elution with ether-pentane 1:1 gave recovered tosylate starting material (8.08 g, 54%).

C. 1,2-Dihydroxyheptane

A solution of the title B ketal (1.87 g, 11.8 mmol) in methanol (30 ml) and concentrated HCl (2.5 ml) was stirred at room temperature 3 hours. The solution was basified by adding concentrated $NH_4OH$ solution (10 ml) and the solvent was removed in vacuo. Saturated NaCl solution (50 ml) was added to the residue and the product was extracted into ether (4×50 ml). The combined ether extracts were washed with saturated NaCl solution (50 ml), dried ($MgSO_4$) and freed of solvent in vacuo leaving the title C diol as a yellow oil (1.13 g, 81%) 13-C NMR consistent. TLC:silica gel, Et$_2$O, vanillin, R$_f$=0.25.

D. 1-Tosyloxy-2-hydroxyheptane

The title C diol (1.13 g, 9.6 mmol) was dissolved in dry pyridine (5 ml) in an argon atmosphere. The solution was cooled to −15° C. and tosyl chloride (2.02 g, 10.6 mmol) was added portionwise in 30 minutes. After addition was complete, stirring was continued at −15° C. for 30 minutes and then the mixture was allowed to warm to room temperature and poured into ice water (60 ml). The product was extracted into ether (3×50 ml) and washed with 1N HCl (2×40 ml), water (40 ml), saturated NaHCO$_3$ solution (40 ml) and saturated NaCl solution (40 ml), dried (MgSO$_4$) and freed of solvent in vacuo leaving 2.56 g oil. This was chromatographed on silica gel 60 (120 g) eluting with ether-pet ether 1:2 and 1:1 to give title D tosylate (1.48 g, 56.7%) TLC silica gel, Et$_2$O-pet ether 1:1, UV and vanillin. R$_f$=0.40. Also obtained from the column was 0.44 g of the ditosylate (R$_f$=0.53) and 0.35 g of a mixture of title D tosylate and the secondary tosylate (R$_f$=0.28).

E. 1-Azido-2-hydroxyheptane

The title D tosylate (1.48 g, 5.44 mmol) was dissolved in dry DMF (20 ml) in an argon atmosphere. Sodium azide (1.6 g, 25 mmol) was added and the mixture was heated at 80°±5° C. for 1 hour. After cooling the mixture was poured into water (50 ml) and extracted with ether (2×100 ml). The combined ether extracts were washed with water (50 ml), dried (Na$_2$SO$_4$) and freed of solvent in vacuo leaving azide as a yellow oil (0.85 g). 13-C NMR is consistent for the title E structure but shows a small amount of DMF. TLC-silica gel, Et$_2$O-pet ether 1:1, PMA R$_f$=0.63. The material was used without purification.

F. 1-Amino-2-hydroxyheptane

The title E azide (∼5.4 mmol) was dissolved in EtOH (100 ml), treated with 5% Pd/Carbon (400 mg) and hydrogenated at up to 47 psi for 2.5 hours. The catalyst was removed by filtration through celite and the solvent was removed in vacuo leaving title F amino alcohol as an oil (0.53 g, 83% from tosylate). TLC-silica gel 10% MeOH in CH$_2$Cl$_2$, PMA R$_f$=∼0.04.

G. [1β,2α(5Z),3α,4β]-7-[3-Formyl-7-oxabicyclo[2.2.1-]hept-2-yl]-5-heptenoic acid, methyl ester A solution of pyridine (14.3 ml, 177 mmol) in dichloromethane (500 ml) was treated portionwise with chromium trioxide (8.9 g, 8.9 mmoles) with vigorous stirring. After addition was complete, the mixture was stirred at room temperature for 30 minutes, then treated with celite (30 g), then [1β,2α(5Z),3α,4β]-7-[3-(hydroxymethyl)-7-oxabicyclo[2.2.1]hept-2-yl]-5-heptenoic acid, methyl ester prepared as described in U.S. Pat. No. 4,143,054 (4 g, 14.96 mmoles) in dichloromethane (20 ml) was added dropwise over a 20 minute period. The reaction mixture was stirred at room temperature for 30 minutes then filtered through celite. The filtrate was washed with 5% sodium bicarbonate (2×250 ml), 10% hydrochloric acid (2×100 ml) and again with 5% sodium bicarbonate (2×250 ml). The dichloromethane solution was dried over magnesium sulfate, filtered and concentrated in vacuo. A brownish residue was dissolved in ether and passed through a pad of Baker silica gel, then eluted with more ether and the ether solution was taken to dryness in vacuo leaving 3.86 g of colorless oil.

H. [1β,2α(5Z),3α,4β]-7-[3-[[(2-Hydroxyhexyl)amino]methyl]-7-oxabicyclo[2.2.1]hept-2-yl]-5-heptenoic acid, methyl ester A solution of title G aldehyde (1.11 g, 4.17 mmol) and title F amino alcohol (0.53 g, 4.53 mmol) in methanol (50 ml) in an argon atmosphere was treated with NaCNBH$_3$ (0.263 g, 4.17 mmol). After cooling the reaction mixture in an ice-bath HOAc (7 ml) was added dropwise. The cooling bath was removed and the mixture was stirred at room temperature for 3 hours. The mixture was acidified to pH 1 by adding 1N HCl solution and stirring was continued 1 hour. A small amount of water was added and solid NaHCO$_3$ was added to basify. The product was extracted into ethyl acetate (4×100 ml) and washed with saturated NaCl solution (100 ml), dried (MgSO$_4$) and freed of solvent in vacuo leaving a viscous oil (1.8 g) which gave a positive boron flame test. This was dissolved in methanol, treated with 1N HCl solution (7 ml) and taken to dryness in vacuo. Methanol was added and removed in vacuo six times to give an oil (1.39 g) which was negative to the boron test. This was chromatographed on SiliCAR CC-7 (100 g) eluting with 2–5% MeOH in CH$_2$Cl$_2$ to give the title H methyl ester as an oil (0.849 g, 55%). TLC-silica gel, 10% MeOH in CH$_2$Cl$_2$+trace NH$_4$OH, vanillin:R$_f$=0.29.

EXAMPLE 2

[1β,2α(5Z),3α,4β]-7-[3-[[(2-Hydroxyhexyl)amino]methyl]-7-oxabicyclo[2.2.1]hept-2-yl]-5-heptenoic acid The Example 1 methyl ester (304 mg, 0.82 mmol) was hydrolyzed in an argon atmosphere by dissolving in THF (25 ml) and water (6 ml) and treating with 1N LiOH solution (8.2 ml). After stirring at room temperature 6 hours, 1N HCl (8.2 ml) was added (pH∼6) and the mixture was taken to near dryness in vacuo. The residue was dissolved in water and chromatographed on a HP-20 column eluting with a water to acetonitrile gradient to give material appearing clean by TLC (silica gel, 25% MeOH in CH$_2$Cl$_2$+trace NH$_4$OH, vanillin; R$_f$=0.18). These fractions were taken to near dryness in vacuo, dissolved in water and lyophilized to give the title product as a white fluffy amorphous material (201 mg).

Anal. Calcd for C$_{20}$H$_{35}$O$_4$N.0.67H$_2$O: C, 65.70; H, 10.02; N, 3.83; Found: C, 65.70; H, 9.72; N, 3.87

EXAMPLE 3

[1β,2α(5Z),3β,4β]-7-[3-[[(2-Hydroxyhexyl)amino]methyl]-7-oxabicyclo[2.2.1]hept-2-yl]-5-heptenoic acid, methyl ester

A. [1β,2α(5Z),3β,4β]-7-[3-Formyl-7-oxabicyclo[2.2.1-]hept-2-yl]-5-heptenoic acid, methyl ester A solution of pyridine (14.6 ml) in dichloromethane (500 ml) was treated portionwise with chromium trioxide (9.06 g) with vigorous stirring. After addition was complete, the mixture was stirred at room temperature for 30 minutes, then treated with celite (30 g), then [1β,2α(5Z),3β,4β]-7-[3-(hydroxymethyl)-7-oxabicyclo[2.2.1]hept-2-yl]-5-heptenoic acid, methyl ester prepared as described in U.S. Pat. No. 4,143,054 (4.05 g, 15.1 mmoles) in dichloromethane (25 ml) was added over a 20 minute period. The reaction mixture was stirred at room temperature for 30 minutes then filtered through celite. The filtrate was washed with 5% sodium bicarbonate (2×300 ml), 10% hydrochloric acid (2×300 ml) and again with 5% sodium bicarbonate (1×300 ml). The dichloromethane solution was dried over magnesium sulfate and concentrated in vacuo. The residue was dissolved in ether, and filtered through a pad of Baker silica gel, washed with ether and the filtrate taken to dryness in vacuo leaving 3.79 g (92%) of pale yellow oil.

B.
[1β,2α(5Z),3β,4β]-7-[3-[[(2-Hydroxyhexyl)amino]methyl]-7-oxabicyclo[2.2.1]hept-2-yl]-5-heptenoic acid, methyl ester A solution of title A aldehyde (1.11 g, 4.17 mmol) and amino alcohol F (0.53 g, 4.53 mmol) in methanol (50 ml) in an argon atmosphere is treated with NaCNBH$_3$ (0.263 g, 4.17 mmol). Afer cooling the reaction mixture in an ice-bath HOAc (7 ml) is added dropwise. The cooling bath is removed and the mixture is stirred at room temperature for 3 hours. The mixture is acidified to pH 1 by adding 1N HCl solution and stirring is continued 1 hour. A small amount of water is added and solid NaHCO$_3$ is added to basify. The product is extracted into ethyl acetate (4×100 ml) and washed with saturated NaCl solution (100 ml), dried (MgSO$_4$) and freed of solvent in vacuo leaving a viscous oil (1.8 g) which gives a positive boron flame test. This is dissolved in methanol, treated with 1N HCl solution (7 ml) and taken to dryness in vacuo. Methanol is added and removed in vacuo six times to give an oil (1.39 g) which is negative to the boron test. This is chromatographed on SiliCAR CC-7 (100 g) eluting with 2–5% MeOH in CH$_2$Cl$_2$ to give the title B methyl ester as an oil (0.849 g, 55%). TLC-silica gel, 10% MeOH in CH$_2$Cl$_2$+trace NH$_4$OH, vanillin: R$_f$=0.29.

EXAMPLE 4
[1β,2α(5Z),3β,4β]-7-[3-[[(2-Hydroxyhexyl)amino]methyl]-7-oxabicyclo[2.2.1]hept-2-yl]-5-heptenoic acid The Example 3 methyl ester (304 mg, 0.82 mmol) is hydrolyzed in an argon atmosphere by dissolving in THF (25 ml) and water (6 ml) and treating with 1N LiOH solution (8.2 ml). After stirring the reaction mixture at room temperature 6 hours, 1N HCl (8.2 ml) is added (pH~6) and the mixture is taken to near dryness in vacuo. The residue is dissolved in water and chromatographed on a HP-20 column eluting with a water to acetonitrile gradient to give material appearing clean by TLC which is taken to near dryness in vacuo, dissolved in water and lyophilized to give the title product as a white fluffy amorphous material.

EXAMPLE 5
(1β,2β,3α,4β)-7-[3-[[(2-Hydroxyhexyl)amino]methyl]-7-oxabicyclo[2.2.1]hept-2-yl]heptanoic acid

A.
(1β,2β,3β,4β)-7-[3-(Hydroxymethyl)-7-oxabicyclo[2.2.1]hept-2-yl]heptanoic acid, methyl ester To 800 mg (3.0 mmole) of the [1β,2β(5Z),3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.
(1β,2β,3β,4β)-7-[3-Formyl-7-oxabicyclo[2.2.1]hept-2-yl]heptanoic acid, methyl ester To 1.21 g (5.6 mmole, 2.0 equiv.) of pyridinium chlorochromate (PCC) and 20 ml of anhydrous CH$_2$Cl$_2$ was added, under an argon atmosphere, 730 mg (2.8 mmole) of the title A alcohol in 2 ml of CH$_2$Cl$_2$. The reaction was stirred for 2 hours at 25°, diluted with 100 ml of ether, filtered through a pad of florisil, and evaporated to furnish 670 mg (88%) of the title B compound as a white crystalline solid.

C.
(1β,2β,3α,4β)-7-[3-Formyl-7-oxabicyclo[2.2.1]hept-2-yl]heptanoic acid, methyl ester To 800.0 mg of the title B aldehyde in 20 ml of anhydrous methanol under an argon atmosphere at 25° was added 100 mg of sodium methoxide. The reaction was stirred for 2 hours, diluted with 100 ml of saturated ammonium chloride and extracted with four 100 ml portions of ether. The ethereal layer was washed with 50 ml of brine dried over anhydrous magnesium sulfate and concentrated to afford 765.0 mg (98%) of the title C aldehyde.

D.
(1β,2β,3α,4β)-7-[3-[[(2-Hydroxyhexyl)amino]methyl]-7-oxabicyclo[2.2.1]hept-2-yl]heptanoic acid Following the procedure of Example 1, except substituting the Part C aldehyde for the Example 1G aldehyde, the title product is obtained.

EXAMPLE 6
[1β,2α(5Z),3α,4β]-7-[3-[[(2-Hydroxypentyl)amino]methyl]-7-oxabicyclo[2.2.1]hept-2-yl]-5-heptenoic acid Following the procedure of Examples 1 and 2 except substituting 1-amino-2-hydroxypentane for 1-amino-2-hydroxyhexane, the title compound is obtained.

EXAMPLE 7
[1β,2α(5Z),3β,4β]-7-[3-[[(2-Hydroxypentyl)amino]methyl]-7-oxabicyclo[2.2.1]hept-2-yl]-5-heptenoic acid Following the procedure of Examples 3 and 4 except substituting 1-amino-2-hydroxypentane for 1-amino-2-hydroxyhexane, the title compound is obtained.

EXAMPLE 8
(1β,2β,3α,4β)-7-[3-[[(2-Hydroxypentyl)amino]methyl]-7-oxabicyclo[2.2.1]hept-2-yl]heptanoic acid Following the procedure of Example 5 except substituting 1-amino-2-hydroxypentane for 1-amino-2-hydroxyhexane, the title compound is obtained.

EXAMPLE 9
[1β,2α(5Z),3α,4β]-7-[3-[[(2-Hydroxyheptylamino)methyl]-7-oxabicyclo[2.2.1]hept-2-yl]-5-heptenoic acid Following the procedure of Examples 1 and 2 except substituting 1-amino-2-hydroxyheptane for 1-amino-2-hydroxyhexane, the title compound is obtained.

EXAMPLE 10

[1β,2α(5Z),3β,4β]-7-[3-[[(2-Hydroxyheptyl)amino]methyl]-7-oxabicyclo[2.2.1]hept-2-yl]-5-heptenoic acid Following the procedure of Examples 3 and 4 except substituting 1-amino-2-hydroxyheptane for 1-amino-2-hydroxyhexane, the title compound is obtained.

EXAMPLE 11

(1β,2β,3α,4β)-7-[3-[[(2-Hydroxy-2-cyclopentylethyl)amino]methyl]-7-oxabicyclo[2.2.1]hept-2-yl]heptanoic acid Following the procedure of Example 5 except substituting 1-amino-2-hydroxy-2-cyclopentylethane for 1-amino-2-hydroxyhexane, the title compound is obtained.

EXAMPLE 12

[1β,2α(5Z),3α,4β]-7-[3-[[(2-Hydroxy-2-phenylethyl)amino]methyl]-7-oxabicyclo[2.2.1]hept-2-yl]-5-heptenoic acid Following the procedure of Examples 1 and 2 except substituting 1-amino-2-hydroxy-2-phenylethane for 1-amino-2-hydroxyhexane, the title product is obtained.

EXAMPLE 13

[1β,2α(5Z),3β,4β]-7-[3-[[(2-Hydroxy-2-phenylpropyl)amino]methyl]-7-oxabicyclo[2.2.1]hept-2-yl]-5-heptenoic acid Following the procedure of Examples 3 and 4 except substituting 1-amino-2-hydroxy-2-phenylpropane for 1-amino-2-hydroxyhexane, the title product is obtained.

EXAMPLE 14

(1β,2α,3β,4β)-7-[3-[[(2-Hydroxy-3-phenylpropyl)amino]methyl]-7-oxabicyclo[2.2.1]hept-2-yl]heptanoic acid Following the procedure of Examples 5 and 3 except substituting 1-amino-2-hydroxy-3-phenylpropane for 1-amino-2-hydroxyhexane, the title product is obtained.

EXAMPLE 15

[1β,2α(5Z),3α,4β]-7-[3-[[[2-Hydroxy-2-(cyclohexylmethyl)butyl]amino]methyl]-7-oxabicyclo[2.2.1]hept-2-yl]-5-heptenoic acid Following the procedure of Examples 1 and 2 except substituting 1-amino-2-hydroxy-2-(cyclohexylmethyl)butane for 1-amino-2-hydroxyhexane, the title product is obtained.

EXAMPLE 16

[1β,2α(5Z),3β,4β]-7-[3-[[[2-Hydroxy-2-(benzyl)pentyl]amino]methyl]-7-oxabicyclo[2.2.1]hept-2-yl]-5-heptenoic acid Following the procedure of Examples 3 and 4 except substituting 1-amino-2-hydroxy-2-(benzyl)pentane for 1-amino-2-hydroxyhexane, the title product is obtained.

EXAMPLE 17

(1β,2α,3β,4β)-7-[3-[[[2-Hydroxy-4-(phenyl)butyl]amino]methyl]-7-oxabicyclo[2.2.1]hept-2-yl]heptanoic acid Following the procedure of Examples 5 and 1 except substituting 1-amino-2-hydroxy-4-(phenyl)butane for 1-amino-2-hydroxyhexane, the title product is obtained.

EXAMPLE 18

[1β,2α(5Z),3α,4β]-7-[3-[[[2-Hydroxy-2-(cyclohexyl)propyl]amino]methyl]-7-oxabicyclo[2.2.1]hept-2-yl]heptenoic acid Following the procedure of Examples 1 and 2 except substituting 1-amino-2-hydroxy-2-(cyclohexyl)propane for 1-amino-2-hydroxyhexane, the title product is obtained.

EXAMPLE 19

[1β,2α(5Z),3α,4β]-7-[3-[[[2-Hydroxy-2-(cyclopentyl)ethyl]amino]methyl]-7-oxabicyclo[2.2.1]hept-2-yl]-5-heptenoic acid Following the procedure of Examples 1 and 2 except substituting 1-amino-2-hydroxy-2-(cyclopentyl)ethane for 1-amino-2-hydroxyhexane, the title product is obtained.

EXAMPLE 20

{1β,2α,3α,4β)-7-[3-[[[2-Hydroxy-3-ethoxypropyl]amino]methyl]-7-oxabicyclo[2.2.1]hept-2-yl]heptanoic acid Following the procedure of Examples 1 and 2 except substituting 1-amino-2-hydroxy-3-ethoxypropane for 1-amino-2-hydroxyhexane, the title compound is obtained.

EXAMPLE 21

[1β,2α(5Z),3β,4β]-7-[3-[[[2-Hydroxy-2-(phenoxyethyl)propyl]amino]methyl]-7-oxabicyclo[2.2.1]hept-2-yl]-5-heptenoic acid Following the procedure of Examples 3 and 4 except substituting 1-amino-2-hydroxy-2-(phenoxyethyl)propane for 1-amino-2-hydroxyhexane, the title compound is obtained.

EXAMPLE 22

(1β,2α,3α,4β)-7-[3-[[[2-Hydroxy-2-benzylhexyl]amino]methyl]-7-oxabicyclo[2.2.1]hept-2-yl]heptanoic acid Following the procedure of Examples 1 and 2 except substituting 1-amino-2-hydroxy-2-benzylhexane for 1-amino-2-hydroxyhexane, the title product is obtained.

EXAMPLE 23

[1β,2α(5Z),3α,4β]-7-[3-[[[2-Hydroxy-2-(propylthioethyl)pentyl]amino]methyl]-7-oxabicyclo[2.2.1]hept-2-yl]-5-heptenoic acid Following the procedure of Examples 1 and 2 except substituting 1-amino-2-hydroxy-2-(propylthioethyl)pentane for 1-amino-2-hydroxyhexane, the title compound is obtained.

EXAMPLE 24

(1β,2β,3α,4β)-7-[3-[[[2-Hydroxy-2-(benzylthiomethyl)-pentyl]amino]methyl]-7-oxabicyclo[2.2.1]hept-2-yl]heptanoic acid Following the procedure of Example 5 except substituting 1-amino-2-hydroxy-2-(benzylthiomethyl)pentane for 1-amino-2-hydroxyhexane, the title product is obtained.

EXAMPLE 25

[1β,2α(5Z),3β,4β]-7-[3-[[[2-Hydroxy-8-(phenylthio)octyl]amino]methyl]-7-oxabicyclo[2.2.1]hept-2-yl]-5-heptenoic acid Following the procedure of Examples 3 and 4 except substituting 1-amino-2-hydroxy-8-(phenylthio)octane for 1-amino-2-hydroxyhexane, the title compound is obtained.

EXAMPLE 26

[1β,2α(5Z),3α,4β]-7-[(2-Hydroxyheptyl)amino]-7-oxabicyclo[2.2.1]hept-2-yl]-5-heptenoic acid

A.

[1β,2α(5Z),3α,4β]-7-[3-Carboxyl-7-oxabicyclo[2.2.1]hept-2-yl]-5-heptenoic acid, methyl ester A solution of 5.0 g (18.66 mmol) of [1β,2α(5Z),3α,4β]-7-[3-(hydroxymethyl)-7-oxabicyclo[2.2.1]hept-2-yl]-5-heptenoic acid, methyl ester in 500 ml of acetone was cooled in an ice-bath. To the above stirred solution was added dropwise 11.4 ml of a 2.67M solution of Jones' reagent. On this scale, the addition required 18 minutes and the reaction mixture was maintained at 0°-5° C. The reaction mixture was allowed to warm to room temperature and stirred for one hour. Isopropyl alcohol (2 ml) was added to destroy excess oxidant. Sodium acetate (20 g) and anhydrous magnesium sulfate was then added to the reaction mixture. This mixture was filtered through a 2" pad of celite and the filtrate was concentrated in vacuo to afford a two-phase residue. The residue was dissolved in ether, dried over anhydrous magnesium sulfate, filtered and concentrated in vacuo to give 5.42 g of crude title A compound as an oil. Purification was effected by flash chromatography on 80 g of florisil using ether as eluant. This gave 3.78 g (72%) of title A compound which solidified on standing in the freezer. Further elution of the above column with ethyl acetate afforded an additional 0.68 g (12%) of title A compound. TLC: silica gel, ether, $R_f$=0.30, iodine.

B.

[1β,2α(5Z),3α,4β]-7-[3-Amino-7-oxabicyclo[2.2.1]hept-2-yl]-5-heptenoic acid, methyl ester To a solution of 5.31 g (18.79 mmol) of title A cis-carboxylic acid in 25 ml of dry benzene containing 8 drops of dry DMF was added dropwise 5.38 ml (61.6 mmol) of oxalyl chloride over a period of 20 minutes. This mixture was stirred at room temperature for 45 minutes and then concentrated in vacuo to provide an orange residue. The residue was dissolved in 200 ml of dry toluene and the resultant solution was heated to 90° C. To this solution was added 3.6 ml (27.12 mmol) of freshly distilled trimethylsilylazide over a period of 25 minutes. The reaction was stirred for 3 hours at 90° C. The reaction mixture was cooled and concentrated in vacuo to provide an orange oil. This residue was dissolved in 125 ml of THF and then added to a stirred solution of 140 ml of 1N aqueous HCl in 1200 ml of THF. The resulting solution was stirred for 12 hours at room temperature and was then concentrated to a volume of 300 ml. The concentrated solution was diluted with 350 ml of distilled water and washed twice with 200 ml of ether. The aqueous layer was neutralized with solid NaHCO₃ and then saturated with solid NaCl. The aqueous layer was extracted with four 50 ml portions of ethyl acetate. The combined ethyl acetate extracts were dried over anhydrous MgSO₄ and concentrated in vacuo to give 1.9 g (40%) of title B compound as an oil. TLC=silica gel 10% MeOH in CH₂Cl₂, $R_f$=0.1, iodine.

C.

[1β,2α(5Z),3α,4β]-7-[3-[(2-Hydroxyheptyl)amino]-7-oxabicyclo[2.2.1]hept-2-yl]-5-heptenoic acid, methyl ester To a solution of 402 mg (2.33 mmol) of 2(S)-acetoxy-1-heptaldehyde (56% ee; prepared by the method of Just; *Tetrahedron Lett.* 1980, 21, 3667) and 200 mg (0.79 mmol) of title B amine in 5 ml of methanol under an argon atmosphere at 25° C. was added ca. 615 mg of crushed activated 3 Å molecular sieves. This mixture was stirred for 48 hours at 25° C., cooled to 0° C., and then an excess of sodium borohydride (156 mg) was added. This mixture was stirred for 33 minutes, quenched with 2 ml of acetone, diluted with 100 ml of ether and washed successively with two 30 ml portions of water, and 30 ml of brine. The organic layer was dried over anhydrous magnesium sulfate and concentrated in vacuo. This material was purified by flash chromatography on 44.2 g of silica gel 60 using initially 1% CH₃OH in CH₂Cl₂ (240 ml) as eluant followed by 3% CH₃OH in CH₂Cl₂. This gave 192 mg of the title methyl ester (60%). TLC: silica gel, 4% CH₃OH in CH₂Cl₂, $R_f$=0.50, iodine.

D.

[1β,2α(5Z),3α,4β]-7-[3-[(2-Hydroxyheptyl)amino]-7-oxabicyclo[2.2.1]hept-2-yl]-5-heptenoic acid To a stirred solution of 192 mg (0.47 mmol) of the Part C methyl ester in 7.40 ml of THF and 1.80 ml of water under argon was added 2.22 ml of 1N aqueous lithium hydroxide solution. Methanol was added to clarify the mixture and the resulting solution was stirred at 25° C. for 25 hours. The reaction mixture was then heated to 50° C. for 1 hour followed by heating at 75° C. for 4 hours. The reaction mixture was cooled, acidified with 1N aqueous HCl solution to pH 5 and concentrated in vacuo. The resulting aqueous solution was saturated with NaCl and washed with EtOAc (3×20 ml). The combined EtOAc extracts were dried (MgSO₄) and concentrated in vacuo to give 172 mg of crude acid. Purification was effected by flash chromatography on 24 g of silica CC-7 using 10% CH₃OH in CH₂Cl₂ as eluant to give the N-acetyl of the title product (50 mg, 27%) and 63 mg of title product (40%). TLC: silica gel, 10% MeOH in CH₂Cl₂, $R_f$=0.15, iodine; $[\alpha]_D^{23}$=+7.85.

Anal. Calc'd for $C_{20}H_{35}NO_4$: C, 67.99; H, 9.92; N, 3.97 Calc'd for $C_{20}H_{35}NO_4 \cdot 0.50$ mole $H_2O$: C, 66.26; H, 10.01; N, 3.86; Found: C, 66.17; H, 9.71; N, 3.83

EXAMPLE 27

[1β,2α(5Z),3α,4β]-7-[3-[(2-Hydroxypentyl)amino]-7-oxabicyclo[2.2.1]hept-2-yl]-5-heptenoic acid Following the procedure of Example 26 except substituting 2(S)-acetoxy-1-pentaldehyde for 2(S)-acetoxy-1-heptaldehyde, the title compound is obtained.

EXAMPLE 28

[1β,2α(5Z),3α,4β]-7-[3-[(2-Hydroxy-2-phenylethyl)amino]-7-oxabicyclo[2.2.1]hept-2-yl]-5-heptenoic acid Following the procedure of Example 26 except substituting 2(S)-acetoxy-2-phenyl-1-acetaldehyde for 2(S)-acetoxy-1-heptaldehyde, the title compound is obtained.

EXAMPLE 29

[1β,2α(5Z),3α,4β]-7-[3-[(2-Hydroxy-2-cyclohexylethyl)amino]-7-oxabicyclo[2.2.1]hept-2-yl]-5-heptenoic acid Following the procedure of Example 26 except substituting 2(S)-acetoxy-2-cyclohexyl-1-acetaldehyde for 2(S)-acetoxy-1-heptaldehyde, the title compound is obtained.

EXAMPLE 30

[1β,2α(5Z),3α,4β]-7-[3-[(2-Hydroxy-4-phenylbutyl)amino]-7-oxabicyclo[2.2.1]hept-2-yl]-5-heptenoic acid Following the procedure of Example 26 except substituting 2(S)-acetoxy-4-phenyl-1-butyraldehyde for 2(S)-acetoxy-1-heptaldehyde, the title compound is obtained.

EXAMPLE 31

[1β,2α(5Z),3α,4β]-7-[3-[[2-Hydroxy-2-(1-methyl)cyclohexylethyl]amino]-7-oxabicyclo[2.2.1]hept-2-yl]-5-heptenoic acid Following the procedure of Example 26 except substituting 2(S)-acetoxy-2-(1-methyl)cyclohexyl-1-acetaldehyde for 2(S)-acetoxy-1-heptaldehyde, the title compound is obtained.

EXAMPLE 32

[1β,2α(5Z),3α,4β]-7-[3-[[(2-Hydroxy-3-ethoxypropyl)amino]-7-oxabicyclo[2.2.1]hept-2-yl]-5-heptenoic acid Following the procedure of Example 26 except substituting 2(S)-acetoxy-3-ethoxy-1-propionaldehyde for 2(S)-acetoxy-1-heptaldehyde, the title compound is obtained.

EXAMPLE 33

[1β,2α(5Z),3α,4β]-7-[3-[(2-Hydroxy-4-propylthiobutyl)amino]-7-oxabicyclo[2.2.1]hept-2-yl]-5-heptenoic acid Following the procedure of Example 26 except substituting 2(S)-acetoxy-4-propylthio-1-butyraldehyde for 2(S)-acetoxy-1-heptaldehyde, the title compound is obtained.

EXAMPLE 34

[1β,2α(5Z),3α,4β]-7-[3-[(2-Hydroxy-2-cyclohexylpropyl)amino]-7-oxabicyclo[2.2.1]hept-2-yl]-5-heptenoic acid Following the procedure of Example 26 except substituting 2(S)-acetoxy-2-cyclohexyl-1-propionaldehyde for 2(S)-acetoxy-1-heptaldehyde, the title compound is obtained.

EXAMPLE 35

[1β,2α(5Z),3α,4β]-7-[3-[(2-Hydroxy-2-ethyl-1-propyl)amino]-7-oxabicyclo[2.2.1]hept-2-yl]-5-heptenoic acid Following the procedure of Example 26 except substituting 2(S)-acetoxy-2-ethyl-1-propionaldehyde for 2(S)-acetoxy-1-heptaldehyde, the title compound is obtained.

EXAMPLE 36

[1β,2α(5Z),3α,4β]-7-[3-[[2-Hydroxy-2-phenyl-1-butyl)amino]-7-oxabicyclo[2.2.1]hept-2-yl]-5-heptenoic acid Following the procedure of Example 26 except substituting 2(S)-acetoxy-2-phenyl-1-butyraldehyde for 2(S)-acetoxy-1-heptaldehyde, the title compound is obtained.

EXAMPLE 37

[1β,2α(5Z),3α,4β]-7-[3-[[(2-Hydroxyhexyl)amino]ethyl]-7-oxabicyclo[2.2.1]hept-2-yl]-5-heptenoic acid

A.

[1β,2α(5Z),3α,4β]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added 12.9 g (37.7 mmoles) methoxymethyltriphenylphosphonium chloride ((C6H5)3P+—CH2OCH3Cl−) and 235 ml distilled toluene (stored over molecular sieves). The resulting suspension was stirred in an ice bath under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH4Cl and extracted with ether (4×200 ml). The combined ether phases were washed with NaCl, saturated solution, and dried (MgSO4) and concentrated to yield a yellow oil in a white crystalline solid (phosphine oxide). The white solid was triturated with EtOAc and purified by TLC on an LP-1 silica column. The fractions obtained were (A) [1β,2α(5Z),3α,4β]-7-[3-(2-oxo)ethyl-7-oxabicyclo[2.2.1]hept-2-yl]-5-heptenoic acid, methyl ester, (B) [1β,2α(5Z),3α,4β]-7-[3-(2-methoxy)ethenyl-7-oxabicyclo[2.2.1]hept-2-yl]-5-heptenoic acid, methyl ester, and (C) [1β,2α(5Z),3α,4β]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1β,2α(5Z),3α,4β]-7-[3-[[(2-Hydroxyhexyl)amino]ethyl]-7-oxabicyclo[2.2.1]hept-2-yl]-5-heptenoic acid Following the procedures of Examples 1 and 2 except substituting the part A aldehyde for the Example 1, Part G aldehyde, the title compound is obtained.

EXAMPLE 38

[1β,2α(5Z),3β,4β]-7-[3-[[(2-Hydroxyhexyl)amino]ethyl]-7-oxabicyclo[2.2.1]hept-2-yl]-5-heptenoic acid Following the procedure of Example 37, except substituting [1β,2α(5Z),3β,4β]-7-[3-formyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

EXAMPLE 39

[1β,2β(5Z),3α,4β]-7-[3-[[(2-Hydroxyhexyl)amino]ethyl]-7-oxabicyclo[2.2.1]hept-2-yl]-5-heptenoic acid Following the procedure of Example 37, except substituting [1β,2β(5Z),3α,4β]-7-[3-formyl-7-oxabicyclo[2.2.1]hept-2-yl]-5-heptenoic acid, methyl ester (prepared as described in U.S. Pat. No. 4,143,054) for [1β,2α(5Z),3α,4β]-7-[3-formyl-7-oxabicyclo[2.2.1]hept-2-yl]-5-heptenoic acid, methyl ester, the title compound is obtained.

EXAMPLE 40

[1β,2α(5Z),3α,4β]-7-[3-[[(2-Hydroxypentyl)amino]ethyl]-7-oxabicyclo[2.2.1]hept-2-yl]-5-heptenoic acid Following the procedure of Example 37 except substituting 1-amino-2-hydroxypentane for 1-amino-2-hydroxyhexane, the title compound is obtained.

EXAMPLE 41

[1β,2α(5Z),3β,4β]-7-[3-[[(2-Hydroxypentyl)amino]ethyl]-7-oxabicyclo[2.2.1]hept-2-yl]-5-heptenoic acid Following the procedure of Example 38 except substituting 1-amino-2-hydroxypentane for 1-amino-2-hydroxyhexane, the title compound is obtained.

EXAMPLE 42

(1β,2β,3α,4β)-7-[3-[[(2-Hydroxypentyl)amino]ethyl]-7-oxabicyclo[2.2.1]hept-2-yl]heptanoic acid Following the procedure of Example 39 except substituting 1-amino-2-hydroxypentane for 1-amino-2-hydroxyhexane, the title compound is obtained.

EXAMPLE 43

[1β,2α(5 Z), 3α,4β]-7-[3-[[(2-Hydroxyheptylamino)ethyl]-7-oxabicyclo[2.2.1]hept-2-yl]-5-heptenoic acid Following the procedure of Example 37 except substituting 1-amino-2-hydroxyheptane for 1-amino-2-hydroxyhexane, the title compound is obtained.

EXAMPLE 44

[1β,2α(5Z),3β,4β]-7-[3-[[(2-Hydroxyheptyl)amino]ethyl]-7-oxabicyclo[2.2.1]hept-2-yl]-5-heptenoic acid Following the procedure of Example 38 except substituting 1-amino-2-hydroxyheptane for 1-amino-2-hydroxyhexane, the title compound is obtained.

EXAMPLE 45

(1β,2β,3α,4β)-7-[3-[[(2-Hydroxy-2-cyclopentylethyl)amino]ethyl]-7-oxabicyclo[2.2.1]hept-2-yl]heptanoic acid Following the procedure of Example 39 except substituting 1-amino-2-hydroxy-2-cyclopentylethane for 1-amino-2-hydroxyhexane, the title compound is obtained.

EXAMPLE 46

[1β,2α(5Z),3α,4β]-7-[3-[[(2-Hydroxy-2-phenylethyl)amino]ethyl]-7-oxabicyclo[2.2.1]hept-2-yl]-5-heptenoic acid Following the procedure of Example 37 except substituting 1-amino-2-hydroxy-2-phenylethane for 1-amino-2-hydroxyhexane, the title product is obtained.

EXAMPLE 47

[1β,2α(5Z),3β,4β]-7-[3-[[(2-Hydroxy-2-phenylpropyl)amino]ethyl]-7-oxabicyclo[2.2.1]hept-2-yl]-5-heptenoic acid Following the procedure of Example 38 except substituting 1-amino-2-hydroxy-2-phenylpropane for 1-amino-2-hydroxyhexane, the title product is obtained.

EXAMPLE 48

(1β,2α,3β,4β)-7-[3-[[(2-Hydroxy-3-phenylpropyl)amino]ethyl]-7-oxabicyclo[2.2.1]hept-2-yl]heptanoic acid Following the procedure of Example 39 except substituting 1-amino-2-hydroxy-3-phenylpropane for 1-amino-2-hydroxyhexane, the title product is obtained.

EXAMPLE 49

[1β,2α(5Z),3α,4β]-7-[3-[[[2-Hydroxy-2-(cyclohexylmethyl)butyl]amino]ethyl]-7-oxabicyclo[2.2.1]hept-2-yl]-5-heptenoic acid Following the procedure of Example 37 except substituting 1-amino-2-hydroxy-2-(cyclohexylmethyl)butane for 1-amino-2-hydroxyhexane, the title product is obtained.

EXAMPLE 50

[1β,2α(5Z),3β,4β]-7-[3-[[[2-Hydroxy-2-(benzyl)pentyl]amino]ethyl]-7-oxabicyclo[2.2.1]hept-2-yl]-5-heptenoic acid Following the procedure of Example 38 except substituting 1-amino-2-hydroxy-2-benzylpentane for 1-amino-2-hydroxyhexane, the title product is obtained.

EXAMPLE 51

(1β,2α,3β,4β)-7-[3-[[(2-Hydroxy-4-phenylbutyl)amino]ethyl]-7-oxabicyclo[2.2.1]hept-2-yl]heptanoic acid Following the procedure of Example 39 except substituting 1-amino-2-hydroxy-4-phenylbutane for 1-amino-2-hydroxyhexane, the title product is obtained.

EXAMPLE 52

[1β,2α(5Z),3α,4β]-7-[3-[[(2-Hydroxy-2-cyclohexylpropyl)amino]ethyl]-7-oxabicyclo[2.2.1]hept-2-yl]-5-heptenoic acid Following the procedure of Example 37 except substituting 1-amino-2-hydroxy-2-cyclohexylpropane for 1-amino-2-hydroxyhexane, the title product is obtained.

EXAMPLE 53

[1β,2α(5Z),3α,4β]-7-[3-[[(2-Hydroxy-2-cyclopentylethyl)amino]ethyl]-7-oxabicyclo[2.2.1]hept-2-yl]-5-heptenoic acid Following the procedure of Example 37 except substituting 1-amino-2-hydroxy-2-cyclopentylethane for 1-amino-2-hydroxyhexane, the title product is obtained.

EXAMPLE 54

[1β,2α(5Z),3α,4β]-7-[3-[[[2-Hydroxy-2-(ethoxymethyl)ethyl]amino]ethyl]-7-oxabicyclo[2.2.1]hept-2-yl]-5-heptenoic acid Following the procedure of Example 37 except substituting 1-amino-2-hydroxy-2-(ethoxymethyl)ethane for 1-amino-2-hydroxyhexane, the title compound is obtained.

EXAMPLE 55

[1β,2α(5Z),3β,4β]-7-[3-[[(2-Hydroxy-2-(phenoxyethyl)propyl)amino]ethyl]-7-oxabicyclo[2.2.1]hept-2-yl]-5-heptenoic acid Following the procedure of Example 38 except substituting 1-amino-2-hydroxy-2-(phenoxyethyl)propane for 1-amino-2-hydroxy-2-hexane, the title compound is obtained.

EXAMPLE 56

[1β,2α(5Z),3α,4β]-7-[3-[[(2-Hydroxy-2-benzylhexyl)amino]ethyl]-7-oxabicyclo[2.2.1]hept-2-yl]-5-heptenoic acid Following the procedure of Example 37 except substituting 1-amino-2-hydroxy-2-benzylhexane for 1-amino-2-hydroxyhexane, the title product is obtained.

EXAMPLE 57

[1β,2α(5Z),3α,4β]-7-[3-[[(2-Hydroxy-2-(propylthioethyl)pentyl]amino]ethyl]-7-oxabicyclo[2.2.1]hept-2-yl]-5-heptenoic acid Following the procedure of Example 37 except substituting 1-amino-2-hydroxy-2-(propylthioethyl)pentane for 1-amino-2-hydroxyhexane, the title compound is obtained.

EXAMPLE 58

(1β,2β,3α,4β)-7-[3-[[[2-Hydroxy-2-(benzylthiomethyl)pentyl]amino]ethyl]-7-oxabicyclo[2.2.1]hept-2-yl]heptanoic acid Following the procedure of Example 39 except substituting 1-amino-2-hydroxy-2-(benzylthiomethyl)pentane for 1-amino-2-hydroxyhexane, the title product is obtained.

EXAMPLE 59

[1β,2α(5Z),3β,4β]-7-[3-[[[2-Hydroxy-8-(phenylthio)octyl]amino]ethyl]-7-oxabicyclo[2.2.1]hept-2-yl]-5-heptenoic acid Following the procedure of Example 38 except substituting 1-amino-2-hydroxy-8-(phenylthio)octane for 1-amino-2-hydroxyhexane, the title compound is obtained.

EXAMPLE 60

[1β,2α(5Z),3α,4β]-7-[3-[[(2-Hydroxyhexyl)amino]-butyl]-7-oxabicyclo[2.2.1]hept-2-yl]-5-heptenoic acid

A.

[1β,2α(5Z),3α,4β]-7-[3-(3-Oxopropyl)-7-oxabicyclo[2.2.1]hept-2-yl]-5-heptenoic acid, methyl ester

[1β,2α(5Z),3α,4β]-7-[3-(2-Oxoethyl)-7-oxabicyclo[2.2.1]hept-2-yl]-5-heptenoic acid, methyl ester, is treated with methoxymethyltriphenylphosphonium chloride and potassium t-amylate as in Example 37. The product of this reaction is treated with aqueous trifluoroacetic acid to give [1β,2α(5Z),3α,4β]-7-[3-(3-oxopropyl)-7-oxabicyclo[2.2.1]hept-2-yl]-5-heptenoic acid, methyl ester (aldehyde A).

B.

[1β,2α(5Z),3α,4β]-7-[3-(4-Oxobutyl)-7-oxabicyclo[2.2.1]hept-2-yl]-5-heptenoic acid, methyl ester Aldehyde A is treated as in part A above to yield the title B aldehyde [1β,2α(5Z),3α,4β]-7-[3-(4-oxobutyl)-7-oxabicyclo[2.2.1]hept-2-yl]-5-heptenoic acid, methyl ester.

C.

[1β,2α(5Z),3α,4β]-7-[3-[[(2-Hydroxyhexyl)amino]-butyl]-7-oxabicyclo[2.2.1]hept-2-yl]-5-heptenoic acid Following the procedure of Examples 1 and 2 except substituting the Part B aldehyde for the Example 1, Part G aldehyde, the title compound is obtained.

EXAMPLE 61

[1β,2α(5Z),3α,4β]-7-[3-[[(2-Hydroxy-3-ethoxypropyl)amino]butyl]-7-oxabicyclo[2.2.1]hept-2-yl]-5-heptenoic acid Following the procedure of Example 60 except substituting 1-amino-2-hydroxy-3-ethoxypropane for 1-amino-2-hydroxyhexane, the title compound is obtained.

EXAMPLE 62

[1β,2α(5Z),3β,4β]-7-[3-[[(2-Hydroxy-2-(propylthioethyl)pentyl]amino]butyl]-7-oxabicyclo[2.2.1]hept-2-yl]-5-heptenoic acid Following the procedure of Example 60 except substituting 1-amino-2-hydroxy-2-(propylthioethyl)pentane for 1-amino-2-hydroxyhexane, the title compound is obtained.

EXAMPLE 63

[1β,2α(5Z),3α,4β]-7-[3-[[(2-Hydroxyheptylamino)-butyl]-7-oxabicyclo[2.2.1]hept-2-yl]-5-heptenoic acid Following the procedure of Example 60 except substituting 1-amino-2-hydroxyheptane for 1-amino-2-hydroxyhexane, the title compound is obtained.

EXAMPLE 64

[1β,2α(5Z),3α,4β]-7-[3-[[(2-Hydroxy-2-phenylethyl)amino]butyl]-7-oxabicyclo[2.2.1]hept-2-yl]-5-heptenoic acid Following the procedure of Example 60 except substituting 1-amino-2-hydroxy-2-phenylethane for 1-amino-2-hydroxyhexane, the title product is obtained.

EXAMPLE 65

[1β,2α(5Z),3α,4β]-7-[3-[[[2-Hydroxy-2-(cyclohexylmethyl)butyl]amino]butyl]-7-oxabicyclo[2.2.1]hept-2-yl]-5-heptenoic acid Following the procedure of Example 60 except substituting 1-amino-2-hydroxy-2-(cyclohexylmethyl)butane for 1-amino-2-hydroxyhexane, the title product is obtained.

EXAMPLE 66

[1β,2α(5Z),3α,4β]-7-[3-[[(2-Hydroxy-2-benzylpentyl)amino]butyl]-7-oxabicyclo[2.2.1]hept-2-yl]-5-heptenoic acid Following the procedure of Example 60 except substituting 1-amino-2-hydroxy-2-benzylpentane for 1-amino-2-hydroxyhexane, the title product is obtained.

EXAMPLE 67

[1β,2α(5Z),3α,4β]-7-[3-[[(2-Hydroxy-2-cyclohexylpropyl)amino]butyl]-7-oxabicyclo[2.2.1]hept-2-yl]-5-heptenoic acid Following the procedure of Example 60 except substituting 1-amino-2-hydroxy-2-cyclohexylpropane for 1-amino-2-hydroxyhexane, the title product is obtained.

EXAMPLE 68

[1β,2α(5Z),3α,4β]-7-[3-[[(2-Hydroxy-2-cyclopentylethyl)amino]butyl]-7-oxabicyclo[2.2.1]hept-2-yl]-5-heptenoic acid Following the procedure of Example 60 except substituting 1-amino-2-hydroxy-2-cyclopentylethane for 1-amino-2-hydroxy hexane, the title product is obtained.

What is claimed is:

1. A compound having the structural formula

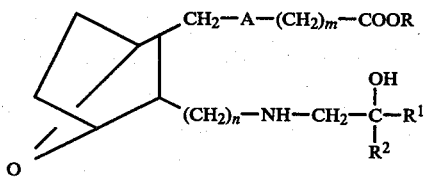

and including all stereoisomers thereof;
wherein A is —CH=CH— or —(CH$_2$)$_2$—;
m is 1 to 8; n is 0 to 5;
R is hydrogen or lower alkyl;
R$^1$ and R$^2$ are the same or different and are selected from the group consisting of hydrogen, lower alkyl, aryl, aralkyl, cycloalkyl, cycloalkylalkyl and —CH$_2$—X—R$^3$ wherein X is O or S and R$^3$ is lower alkyl, aryl or aralkyl, with the proviso that at least one of R$^1$ and R$^2$ is other than hydrogen, wherein the term alkyl or lower alkyl by itself or as part of another group contains 1 to 12 carbons, the term aryl by itself or as part of another group is phenyl or naphthyl and which may be unsubstituted or substituted with a halogen, lower alkyl or lower alkoxy group, and the term cycloalkyl by itself or as part of another group contains 3 to 12 carbon atoms in the ring and may be unsubstituted or substituted with 1 or 2 lower alkyl groups and/or lower alkoxy groups.

2. The compound as defined in claim 1 wherein A is —CH=CH—.

3. The compound as defined in claim 1 wherein R is H.

4. The compound as defined in claim 1 wherein A is —CH=CH—, m is 2 to 4, n is 0 or 1, R$^2$ is H and R$^1$ is lower alkyl, aryl, aralkyl or cycloalkyl.

5. The compound as defined in claim 1 wherein A is —CH=CH—, m is 3, n is 1, R is H or CH$_3$, R$^2$ is H and R$^1$ is lower alkyl.

6. The compound as defined in claim 1 wherein R is H, R$^2$ is H and R$^1$ is —CH$_2$—O—R$^3$ or —CH$_2$—S—R$^3$.

7. The compound as defined in claim 1 having the name [1β,2α(5Z),3α,4β]-7-[3-[[(2-hydroxyhexyl)amino]methyl]-7-oxabicyclo[2.2.1]-hept-2-yl]-5-heptenoic acid or the methyl ester thereof.

8. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

9. The method as defined in claim 8 wherein said compound is administered in an amount within the range of from about 1 to about 100 mg/kg.

10. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

11. A method of inhibiting platelet aggregation which comprises administering to a mammalian host an effective amount of a compound as defined in claim 1 or a pharmaceutically acceptable salt thereof.

12. A method of inhibiting bronchoconstriction associated with asthma, which comprises administering to a mammalian host an effective amount of a compound as defined in claim 1 or a pharmaceutically acceptable salt thereof.

13. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,456,616
DATED : June 26, 1984
INVENTOR(S) : Martin F. Haslanger

It is certified that error appears in the above—identified patent and that said Letters Patent is hereby corrected as shown below:

On the title page, the name of the first inventor should read --Martin F. Haslanger--.
Column 5, after structure IB and before line 61, insert --where n is 2 to 5--.
Column 8, the structures on lines 47-67 should read as follows:

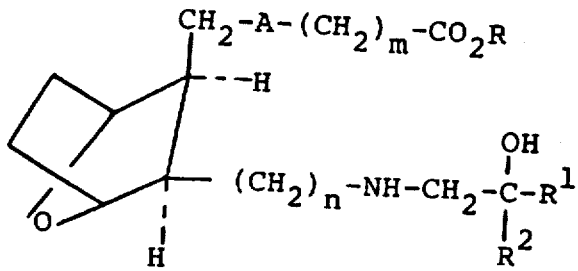

Ia (cis-endo)

UNITED STATES PATENT AND TRADEMARK OFFICE
CERTIFICATE OF CORRECTION

PATENT NO. : 4,456,616
DATED : June 26, 1984
INVENTOR(S) : Martin F. Haslanger et al.

It is certified that error appears in the above—identified patent and that said Letters Patent is hereby corrected as shown below:

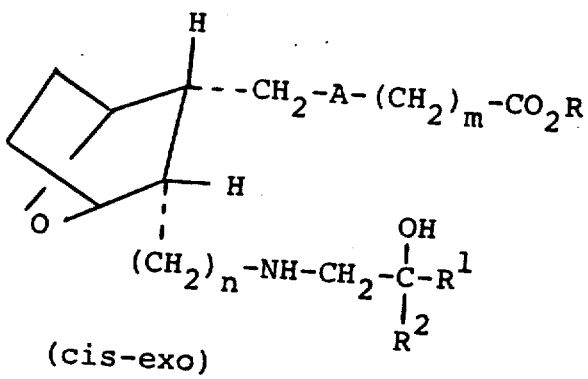

(cis-exo)      Ib

Column 9, the first two structures should read:

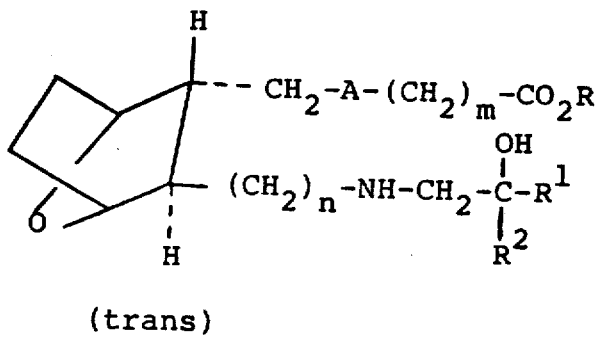

(trans)

UNITED STATES PATENT AND TRADEMARK OFFICE
CERTIFICATE OF CORRECTION

PATENT NO. : 4,456,616

DATED : June 26, 1984

INVENTOR(S) : Martin F. Haslanger et al.

It is certified that error appears in the above—identified patent and that said Letters Patent is hereby corrected as shown below:

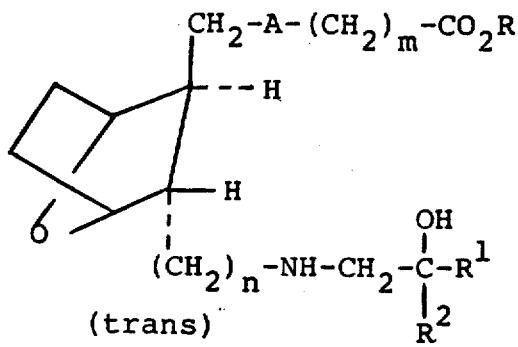

Signed and Sealed this

Second Day of April 1985

[SEAL]

Attest:

DONALD J. QUIGG

Attesting Officer     Acting Commissioner of Patents and Trademarks